(12) United States Patent
Tallarida et al.

(10) Patent No.: US 6,962,577 B2
(45) Date of Patent: Nov. 8, 2005

(54) IMPLANTABLE HEMODIALYSIS ACCESS DEVICE

(75) Inventors: Steven J. Tallarida, Mansfield, MA (US); Mark Ettlinger, Lexington, MA (US)

(73) Assignee: STD Manufacturing, Inc., Stoughton, MA (US)

( * ) Notice: Subject to any disclaimer, the term of this patent is extended or adjusted under 35 U.S.C. 154(b) by 412 days.

(21) Appl. No.: 09/842,458

(22) Filed: Apr. 26, 2001

(65) Prior Publication Data

US 2001/0056266 A1 Dec. 27, 2001

Related U.S. Application Data

(60) Provisional application No. 60/199,714, filed on Apr. 26, 2000.

(51) Int. Cl.[7] .................................................. A61M 31/00
(52) U.S. Cl. ................................................. 604/288.02
(58) Field of Search ............ 604/93.01, 288.01–288.04, 604/890.1–891.1, 905, 175, 82

(56) References Cited

U.S. PATENT DOCUMENTS

| | | | |
|---|---|---|---|
| 4,181,132 A | 1/1980 | Parks ........................ 128/399 |
| 4,673,394 A | 6/1987 | Fenton, Jr. et al. ......... 604/175 |
| 4,776,843 A | * 10/1988 | Martinez et al. .............. 604/86 |
| 4,802,885 A | 2/1989 | Weeks et al. ................. 604/93 |
| 4,892,518 A | 1/1990 | Cupp et al. ................... 604/93 |
| 4,969,873 A | * 11/1990 | Steinbach et al. ..... 604/288.02 |
| 5,041,098 A | 8/1991 | Loiterman et al. .......... 604/175 |
| 5,092,849 A | * 3/1992 | Sampson .................... 604/175 |
| 5,203,771 A | 4/1993 | Melker et al. ................. 604/53 |
| 5,213,574 A | 5/1993 | Tucker ......................... 604/93 |
| 5,215,530 A | 6/1993 | Hogan ........................ 604/174 |
| 5,234,406 A | 8/1993 | Drasner et al. ............... 604/51 |
| 5,281,199 A | 1/1994 | Ensminger et al. ........... 604/93 |
| 5,318,545 A | 6/1994 | Tucker ........................ 604/244 |
| 5,350,360 A | 9/1994 | Ensminger et al. ........... 604/93 |
| 5,387,192 A | 2/1995 | Glantz et al. ................. 604/93 |
| 5,399,168 A | 3/1995 | Wadsworth, Jr. et al. ... 604/175 |
| 5,417,656 A | 5/1995 | Ensminger et al. ........... 604/93 |
| 5,520,643 A | 5/1996 | Ensminger et al. ........... 604/93 |
| 5,527,278 A | 6/1996 | Ensminger et al. ........... 604/93 |
| 5,556,381 A | 9/1996 | Ensminger et al. ........... 604/93 |
| 5,558,641 A | 9/1996 | Glantz et al. ................. 604/93 |
| 5,562,617 A | 10/1996 | Finch, Jr. et al. ............. 604/93 |
| 5,562,618 A | 10/1996 | Cai et al. ...................... 604/93 |
| 5,613,945 A | 3/1997 | Cai et al. ...................... 604/93 |
| 5,704,915 A | 1/1998 | Melsky et al. .............. 604/175 |
| 5,718,692 A | 2/1998 | Schon et al. ................ 604/264 |
| 5,792,104 A | 8/1998 | Speckman et al. ............ 604/93 |
| 5,833,654 A | * 11/1998 | Powers et al. ........... 604/93.01 |
| 5,848,989 A | 12/1998 | Villani ......................... 604/93 |
| 5,931,801 A | 8/1999 | Burbank et al. ................ 604/4 |
| 5,954,691 A | 9/1999 | Prosl ............................ 604/93 |
| 5,989,206 A | 11/1999 | Prosl et al. .................... 604/5 |
| 6,007,516 A | 12/1999 | Burbank et al. ............... 604/93 |
| 6,213,973 B1 | * 4/2001 | Eliasen et al. ........... 604/93.01 |

OTHER PUBLICATIONS

Australian Office Action received in corresponding Australian Application No. 2001257388 mailed Jan. 21, 2005.

* cited by examiner

*Primary Examiner*—LoAn H. Thanh
(74) *Attorney, Agent, or Firm*—Grossman Tucker Perreault & Pfleger, PLLC

(57) ABSTRACT

A hemodialysis port comprising a flexible housing member defining one or more ports. Each port has a selectively-permeable septum member disposed thereon to permit medical devices, for example, Huber needles, sheath and/or dilators to be inserted therein. At the interface between the housing and the septum, a spring member is provided to provide an axial force on the septum which seals the puncture created by the aforementioned medical devices. In one exemplary embodiment, the hemodialysis access port of the present invention is comprised of a plurality of ports designed for multiple hemodialysis treatments over the life of the port. In other exemplary embodiments, the bottom of each port may comprise a needle stop insert formed of, for example, metal, titanium, stainless steel or ceramic.

6 Claims, 12 Drawing Sheets

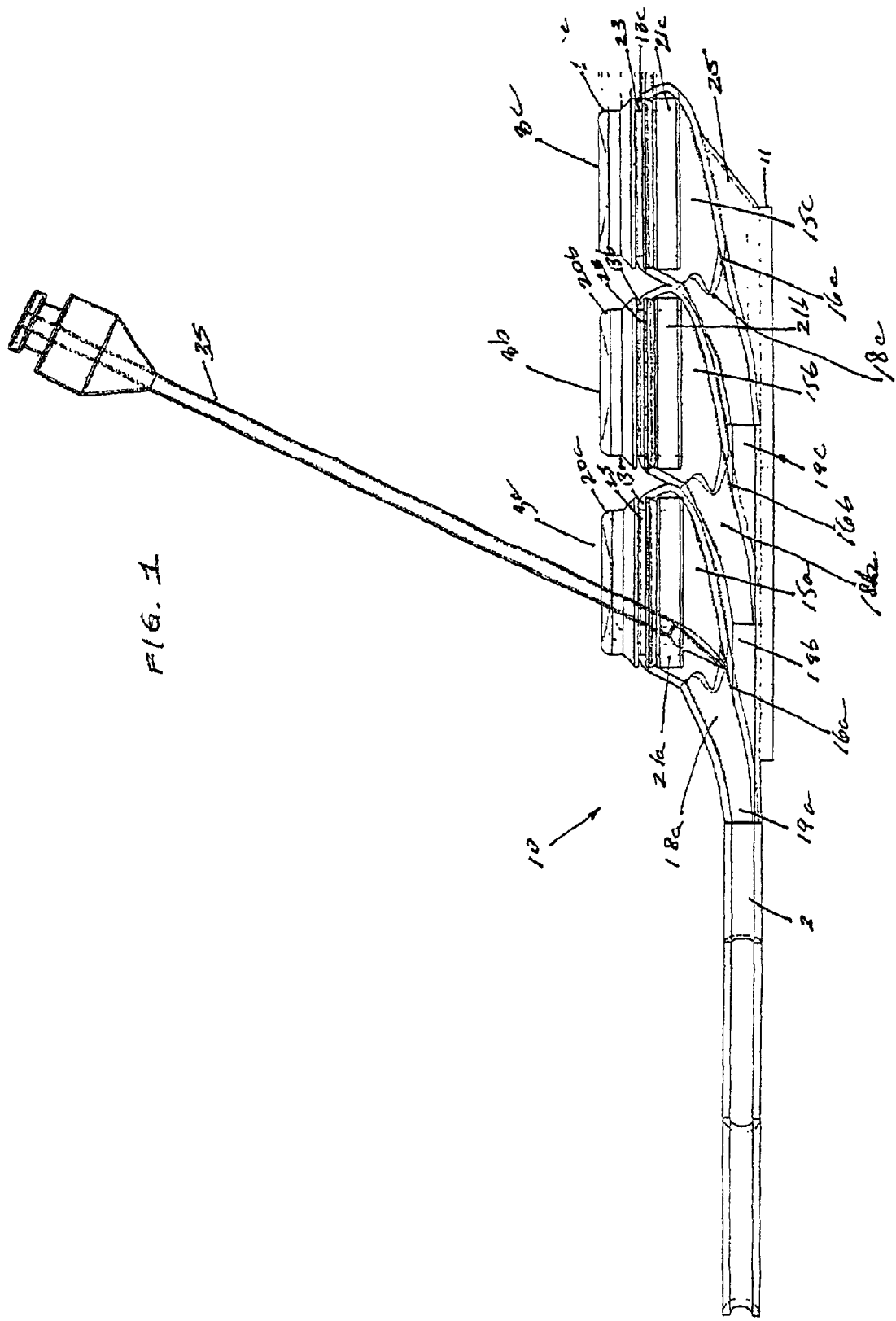

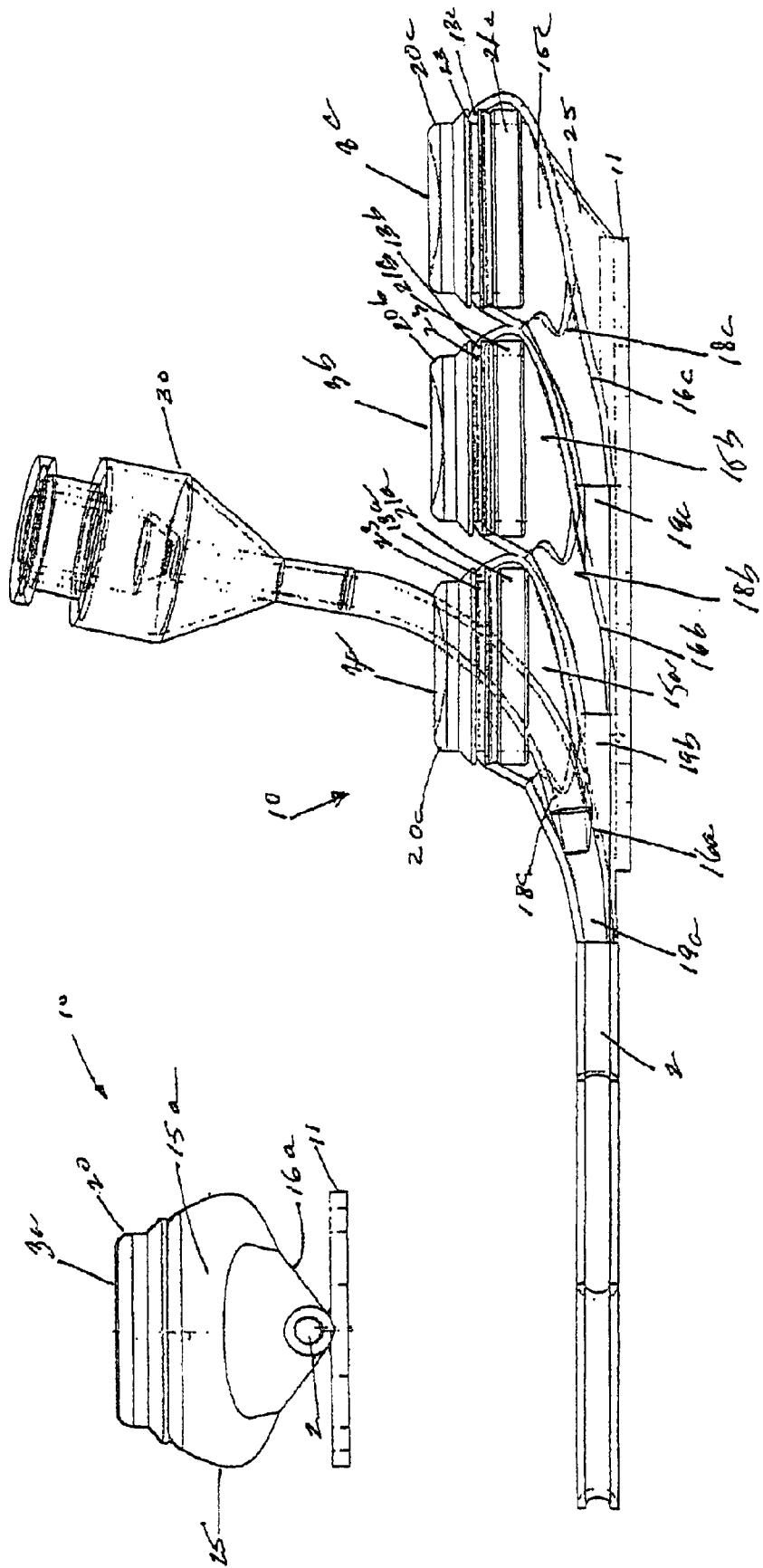

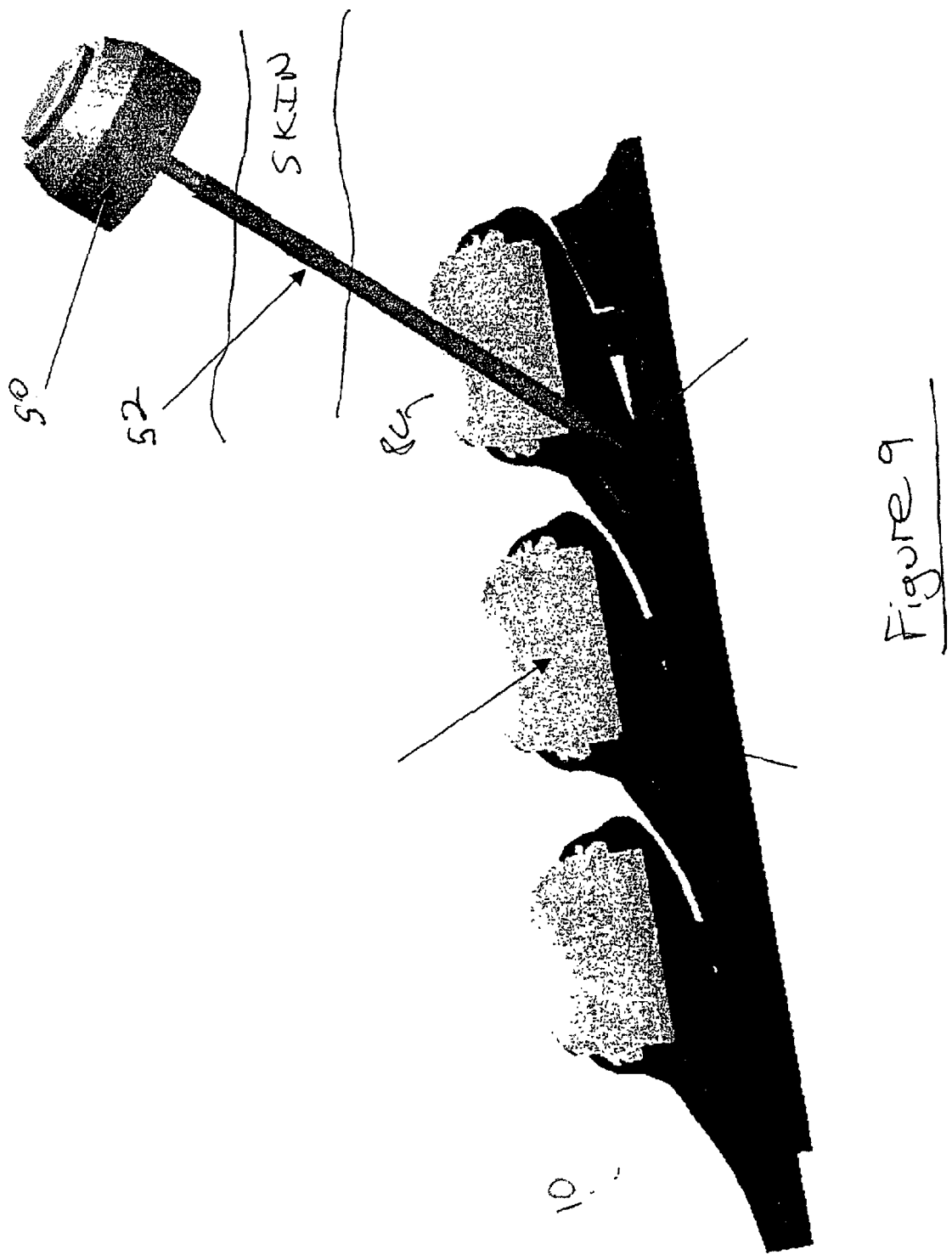

IMPLANTABLE HEMODIALYSIS ACCESS DEVICE

CROSS-REFERENCE TO RELATED APPLICATIONS

This application claims the benefit of U.S. provisional patent application Ser. No. 60/199,714, filed Apr. 26, 2000, the entire disclosure of which is incorporated by reference.

FIELD OF THE INVENTION

The present invention relates to an implantable biocompatible access device used in conjunction with hemodialysis and the delivery of medicants and other fluids into a body, or the withdrawal of fluids from the body.

BACKGROUND OF THE INVENTION

Access to a patient's vascular system can be established by a variety of temporary and permanently implanted devices. Most simply, temporary access can be provided by the direct percutaneous introduction of a needle through the patient's skin and into a blood vessel. While such a direct approach is relatively simple and suitable for applications such as intravenous feeding, intravenous drug delivery, and other applications which are limited in time, they are not suitable for hemodialysis and other extracorporeal procedures that must be repeated periodically, often for the lifetime of the patient.

For hemodialysis and other extracorporeal treatment regimens, a variety of transcutaneous catheters and implantable ports have been proposed over the years. Prior medical transcutaneous catheters comprise a single catheter tube having a distal end placed in a vein in an inu-dwelling manner and a proximal end which extends through the skin and which is available for connection to a hemodialysis or other blood treatment system.

Implantable infusion devices or ports, in contrast, are entirely subcutaneous and connected to a vein to an artery by a subcutaneous cannula. Access to the port is achieved by percutaneous placement of a needle or other connecting tube. Such ports typically comprise a needle-penetrable septum to permit percutaneous penetration of the needle. However, conventional ports do not allow the needle to penetrate deeply into the port. Because of this, a small displacement of the needle can cause it to be pulled from the port. In cases where locally toxic materials are being infused, extravasation of such materials can cause local tissue damage which may require corrective surgery such as skin grafting or removal of tissue. Recently, several valved-port designs have been proposed, where introduction of a needle or other access tube opens a valve to provide flow to the cannula which connects to the blood vessel.

Both the transcutaneous and subcutaneous implanted port vascular access systems described above suffer from certain disadvantages and limitations. For example, both such systems permit only limited blood flow rates. In the case of transcutaneous catheters, the limited flow rates result from the generally small lumen diameters available in in-dwelling catheters. In the case of implanted port access systems, the limited flow rates have resulted from both the port structure and the relatively small lumen diameters available in the cannulas which connect the port to the blood vessel. Such limited blood flow rates are problematic since they prolong the duration of the associated extracorporeal blood treatment protocol, such as hemodialysis, hemofiltration, and apheresis.

The subcutaneous placement of the catheter or cannula which is connected to or implanted within the blood vessel and brought to the external attachment point, i.e., either the implanted port or transcutaneous tract through the skin, is difficult in a number of respects. For, example, catheters and cannulas having their distal ends implanted in the jugular vein are typically bent by an from 90° to 180° to locate their associated ports or catheter exit points at an appropriate location on the patient's chest. Such bends also can accommodate excess length in connecting catheters and cannulas. The bends, however, are also subject to kinking and other problems.

One attempt at solving other problems is found in U.S. Pat. No. 5,387,192 to Glantz, et al. This patent disclosed a subcutaneously implantable access port, includes a two piece plastic jacket, comprised of a cowl and a base, which surrounds a metallic reservoir. The metallic reservoir has an open top and a closed bottom. The open top of the reservoir is sealed by the septum to define a chamber. The non-metallic cowl includes a septum opening and a flange positioned adjacent to the top of the opening. The non-metallic base includes a reservoir opening in which the metallic reservoir is received. The cowl and base are positioned to define a forming zone and are connected at the forming zone to substantially surround the metal reservoir.

One problem encountered such devices having fluid cavities and separate exit passageways through which the fluids will travel, is the formation in such devices of seams, having corners and edges. As blood or other fluids are injected into a fluid cavity, pressure develops within the cavity causing the fluid to flow through the exit passageway. As a result of the fluid flowing past these seams, edges and corners, turbulence may develop, which will affect some fluids, such as blood, which are sensitive to turbulence. A further problem with the reservoir cup is that dead spots are created in the areas where the floor of the cup meets the exit passageway retarding the fluid flow, leading to stagnation or the formation of clots or blockages in the port.

A series of U.S. Patents to William Ensminger, et al., discloses access ports having internal lumens for receiving a percutaneously introduced access device (e.g. a needle or catheter/stylet combination) and internal valve structures for isolating the port from an associated implanted catheter. These patents, disclose a number of specific valve types which may be incorporated within the access port, including leaflet valves, ball valves, flapper valves, and other specific configurations which are referred to as "articulating valves." All such structures, however, generally require that the access device be passed through the valve itself (i.e., the portion which closes the blood flow path through the valve) in order to cause the valve to open. Such a requirement presents the risk that the valve will be degraded by direct contact with the access device after repeated uses so that portions of the valve may be degraded and released into circulation. Such valves also present a significant risk of failure after repeated use or contact with a sharpened needle. Additionally, such valve structures can damage the access device as it is being introduced therethrough, thus potentially disrupting valve flow through the needle during a subsequent treatment protocol.

In U.S. Pat. No. 5,704,915 to Melsky, et al., a dual access port for hemodialysis comprising a pair of conical or funnel-like shells is joined tangentially at their outer surfaces. Each shell having a relatively large entrance and a relatively small exit end. A self-sealing septum closes the entrance of each shell and a pair of outlet tubes extend from the exit ends of each shell. The conical configuration places the septum of each shell opposite the outlet tube so that when a needle accesses the port, it will lie in line with the outlet tube. A bend in the shell prevents the access needles from being advanced to a point where the needles can puncture the walls of the attached catheter. The shells include a carbon insert or liner to create a thromboresistant as well as scratch resistant surface over most of the shell's interior. In the areas which are likely to be contacted by the tip of the needle, pyrolitic carbon coating may be used. The remaining interior surface, for example at the outlet tube, can be titanium.

A problem with the Ensminger and Melsky devices is that the entry ports are usually inclined at a substantial angle relative to the skin surface through which the access device is introduced. Such angled access requires that the personnel introducing the access device guess the angle and estimate the optimum insertion point on the patient's skin. Such uncertainty in the device penetration is perhaps why these designs all require the use of enlarged "funnel" for receiving and aligning the needle as it is introduced. It would thus be advantageous to provide access ports having entry passages which are disposed generally "vertically" (i.e., at an angle which is substantially normal to the skin surface through which the needle is being introduced). By penetrating the needle "straight in," it is much easier to align the needle with the target orifice and the size of the orifice area can be reduced.

Accordingly, there has been a need for an improved an implantable, subcutaneous single or multi-port vascular access device for hemodialysis and other drug delivery applications, which overcomes the above-noted problems.

SUMMARY OF THE INVENTION

Accordingly, the present invention provides an improved hemodialysis access port having a flexible non-metallic housing. In one exemplary embodiment, multiple ports are provided. The multiple ports allow for extended life of the device and less trauma to the tissues. In another embodiment, a single port is provided. Each port includes a circular opening sealed by a self-sealing septum, rubber or silicone, for example, a generally conical or funnel shaped chamber for receiving fluid extends from the circular opening at an angle. The circular opening will be generally parallel to the skin's surface allowing vertical penetration. The funnel section includes an insert formed of, for example, metal, titanium, stainless steel, or ceramic. The insert is molded, pressed or bonded at the base end of the funnel section, leading to an integrated outlet, to serve as a needle stop to prevent potential penetration of needles through the plastic housing. This configuration also permits access by a blunt flexible catheter through the funnel to the outlet.

In specific exemplary embodiments, the present invention provides a hemodialysis port comprising a housing defining a plurality of interconnected chambers, each said chamber having a bottom portion and sidewall portions; a septum attached to said side wall portions of each said chamber enclosing said chamber; and a spring mechanism disposed between said sidewalls and said septum and applying an inward force on said septum.

The present invention also provides a method for performing hemodialysis, comprising the steps of inserting at least one multi-port device under the skin of a patient; inserting a needle and sheath through said skin and into one of said ports of said multi-port device; removing said needle from within said sheath, leaving said sheath in said port; and inserting a cannula and obturator into said sheath and drawing from said cannula blood from within said port.

The present invention also provides a separate hemodialysis method comprising the steps of inserting a multi-port device under the skin of a patient; inserting a hollow needle into one of the ports of said multi-port device through the skin of said patient; inserting a guidewire through said needle and into said port; removing said needle from said port and said patient; and inserting an introducer over said guidewire and into said port.

The individual ports may be connected to a single outlet tube or passage. Alternatively, each port may lead to separate outlet tubes, for example when it is desired that one port be used for infusion while another port be used for withdrawal. Each port has an open center and flanges retains the septum which fits over the top edge of the circular opening of a port and is further retained in the opening by means of a circular wound or "clock" spring configured around its periphery to apply continuous hoop pressure over the life of the port. Each of the septa include identification features incorporated on their upper surfaces to distinguish one from the other.

BRIEF DESCRIPTION OF THE DRAWINGS

FIG. 1 is a cross-sectional view of the exemplary multiple access port according to the present invention;

FIG. 2 is another cross-sectional view of the exemplary multiple access port according to the present invention;

FIG. 3 is a front view of an access port according to the present invention;

FIGS. 9–11 depict one exemplary method of use of the hemodialysis of the present invention.

DETAILED DESCRIPTION OF EXEMPLARY EMBODIMENT

Figure 4:
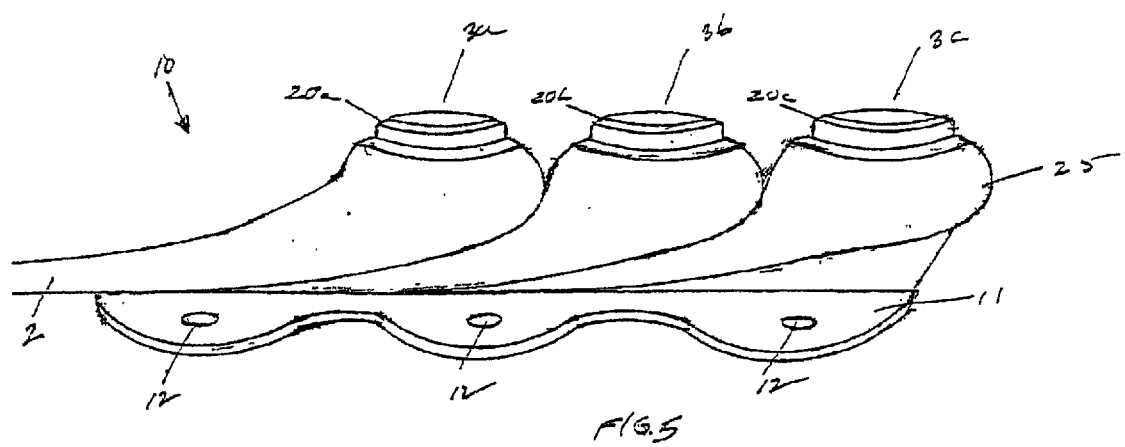
FIG. 4 is a perspective view of the exemplary multiple access port according to the present invention.

FIGS. 1–5, depict various views of the exemplary low-profile multiple port implantable access device 10 of the present invention. The access device 10 generally comprises a housing member 25 including circular openings 5a, 5b and 5c on the upper side of the housing and base 11 on the bottom on the housing. The housing 25 is constructed from a biocompatible non-metallic material, such as plastic, and is moderately flexible as to allow for improved anatomical placement over curved or irregular sections of the fascia musculature. Flexibility, in this sense, is not easily definable since many factors, such as patient anatomical profile data, patient comfort, doctor preference, etc., will go in to determining how flexible the housing should be. Thus, the present invention recognizes that the flexibility spectrum is rather large, and may be determined on a patient-by-patient basis, or may comprise flexibility standards based, on, for example, patient profile data, average patient profile data, etc., and the present invention is intended to cover all such alternatives. The housing 25 and ports 3a, 3b and 3c have circular openings 5a, 5b and 5c, defining fluid chambers 15a, 15b and 15c. The chambers are sealed by the housing 25, and self-sealing septum members 20a, 20b and 20c, arranged in the circular openings. Preferably the septum is constructed of silicone or similar elastomeric material, or rubber. For hemodialysis applications, the septum can have a durometer ranging from 30–55, since it is understood that the septum must withstand several large-diameter insertions while still maintaining fully sealed integrity.

The circular openings 5a, 5b and 5c in ports 3a, 3b and 3c are generally parallel to the skin's surface allowing for substantially vertical penetration of a needle 35 or catheter 30. The fluid chambers 15a, 15b and 15c are generally conical or funnel-shaped and extend at an angle in relation to the circular openings. Such configuration assists in providing better flow characteristics, easy access to each port and enables a low-profile shape.

The funnel sections 18a, 18b and 18c taper (narrow) in diameter as they approach integrated outlet passageways 19a, 19b and 19c respectively. In the exemplary embodiment, integrated outlet passageways 19a, 19b and 19c connect to single outlet tube 2, which delivers fluid out of the chambers 15a, 15b, and 15c and integrated passageways 19a, 19b and 19c to a predetermined location, via stem and attached catheter (not shown), as is understood in the art.

Such connection may be made consecutively with one passageway flowing into another or may be arranged with separate passageways conjoining at or near the outlet tube 2. In another embodiment, the passageways may remain separate, connecting with separate outlet tubes, for example, where one port and passageway is used for infusion or to deliver fluid and another port and passageway for withdrawal.

The funnel sections 18a, 18b and 18c, particularly the bottom portions 16a, 16b and 16c thereof, include a metallic, titanium, stainless steel, for example, or ceramic insert. The insert at the bottom portions, 16a, 16b and 16c are molded, pressed, welded, bonded or attached by other known means, toward the base end of the funnel sections 18a, 18b and 18c, leading to integrated outlet passageways 19a, 19b and 19c, and are of sufficient length and width to serve as a needle stop to prevent potential penetration of needles 35 through port 3a of the access device 10, as shown in FIG. 1. This configuration also permits access by a blunt flexible catheter 30 in port 3a through the funnel 19a to the integrated outlet passageway 18a, shown in FIG. 2.

Figure 5:
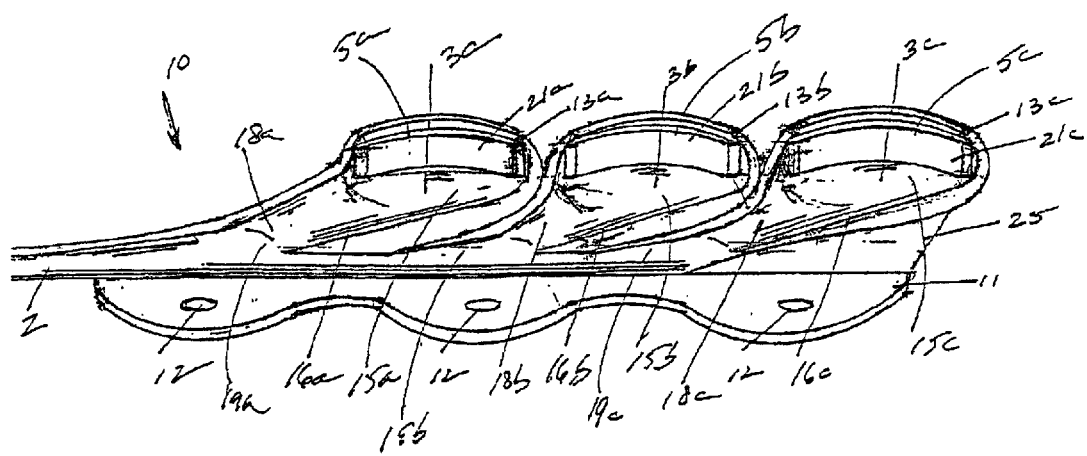
FIG. 5 is a cut-away perspective view of the exemplary multiple access port according to the present invention.

Referring to FIGS. 3–5, can be seen base 11 of housing 25 and integrated suture holes 12 to further secure the implantable access device 10 to the patient. Similar to the housing 25, base 11 is moderately flexible as to allow for improved anatomical placement and securement of the access device 10 over the fascia musculature.

Flow valves (not shown) may be provided on each chamber to prevent back fluid from entering the chamber, i.e., the flow valves may be formed to permit only one direction of fluid travel.

Turning to FIG. 5, is seen ports 3a, 3b and 3c, each port having an open center and flanges 13a, 13b and 13c located around the periphery of the top edge of circular openings 5a, 5b and 5c which engage grooves 23 of septa 20a, 20b and 20c and flanges are dimensioned so as to force against the septum, thereby holding the septum in place. Circular wound or clock springs 21a, 21b and 21c are arranged in the upper portion of chambers 15a, 15b and 15c, respectively, positioned around the periphery and below the circular openings 5a, 5b and 5c of each port. Such springs are configured so as to apply continuous hoop pressure over the life of the access device and in conjunction with the flanges, further retain the septum in the port opening. The springs 21a, 21b and 21c are preferably formed of titanium, stainless steel, ceramic, and/or other biocompatible material.

Figure 6:
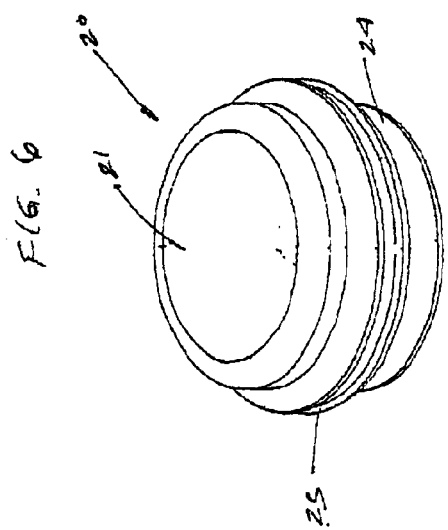
FIG. 6 is a perspective view of a septum according to the present invention.
Figure 8:
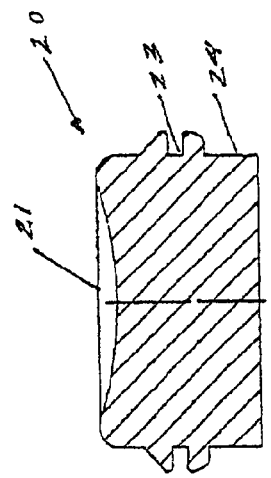
FIG. 8 is a cross-sectional view of a septum according to the present invention.
Figure 7:
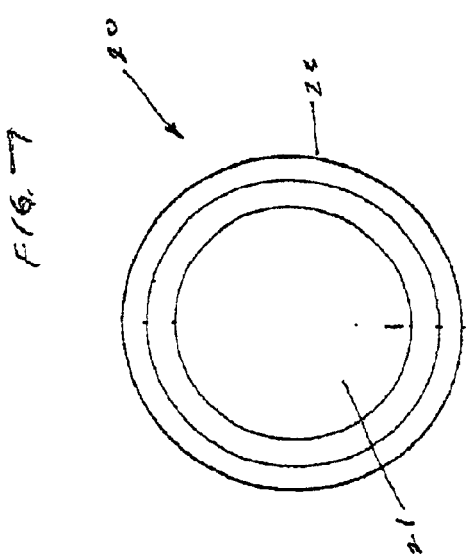
FIG. 7 is a top plan view of a septum according to the present invention.

As best seen in FIGS. 6 and 8, septum 20 is preferably formed of silicon or other semi-permeable materials that permit ingress and egress of needles to deliver fluid to the chambers. In the exemplary embodiment, septums 20, and 20a, 20b and 20c as shown in the drawings, are formed with a generally circular shape, and, may include a nipple or other identification feature incorporated on the upper generally concave surfaces 21 thereof to distinguish one from the other. A nipple or similar raised feature may be advantageous for visual and/or tactile location and identification of each port of the access device 10, but is not necessary for the present invention. In an alternative embodiment, concave surfaces 21 may have an indented or recessed identification feature, where a protruding feature is undesirable. The septums 20, and 20a, 20b and 20c are preferably formed with tongue and groove portions 23, which mate with flanges 13am 13b and 13c located at the top edges of the circular openings 5a, 5b and 5c of the ports 34a, 3b and 3c. The lower portion 24 of the septums 20, 20a, 20b and 20c are sized so as to be held securely against the inner surfaces of clock springs 21a, 21b and 21c.

Figure 10:
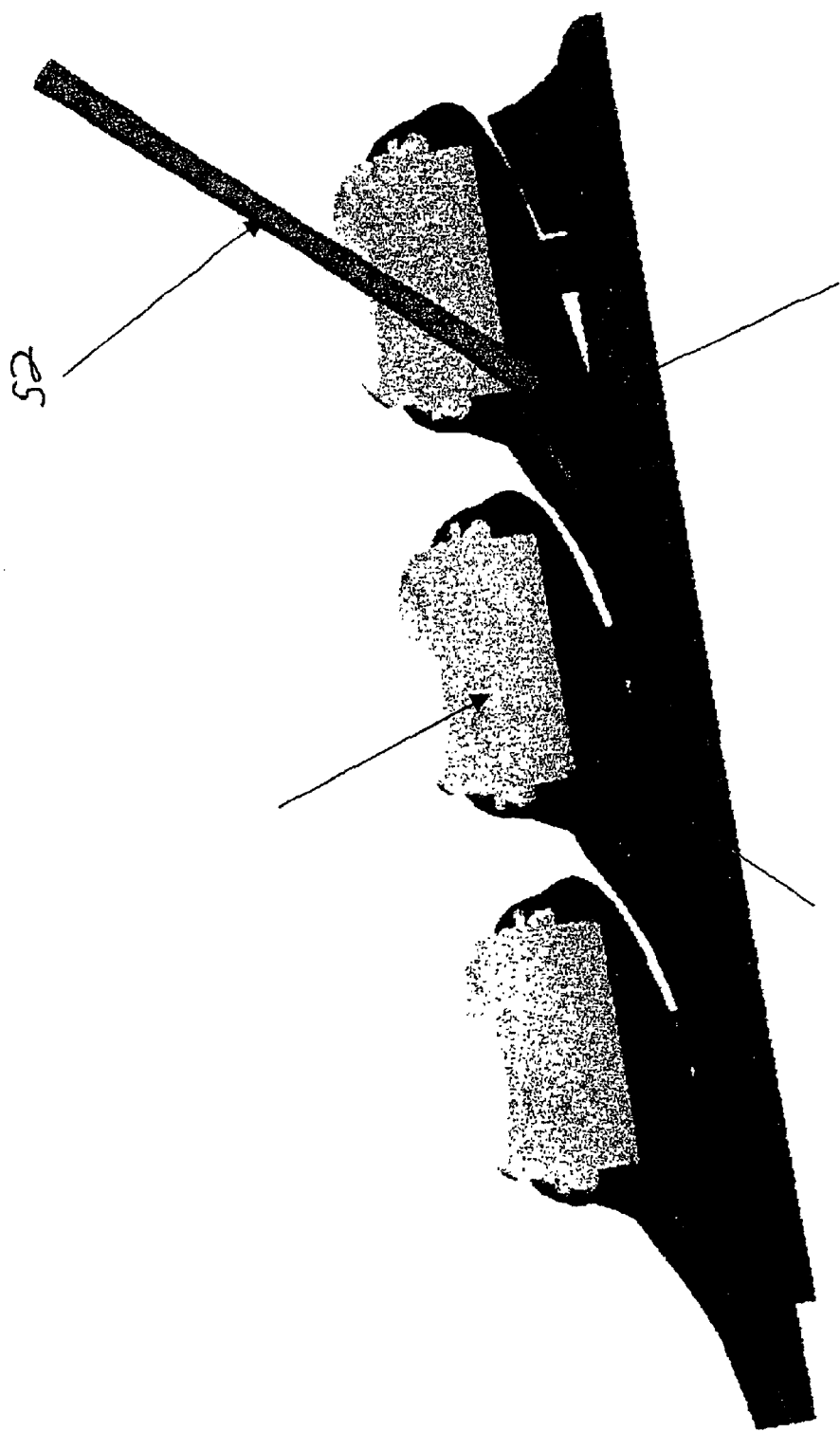
Figure 11:
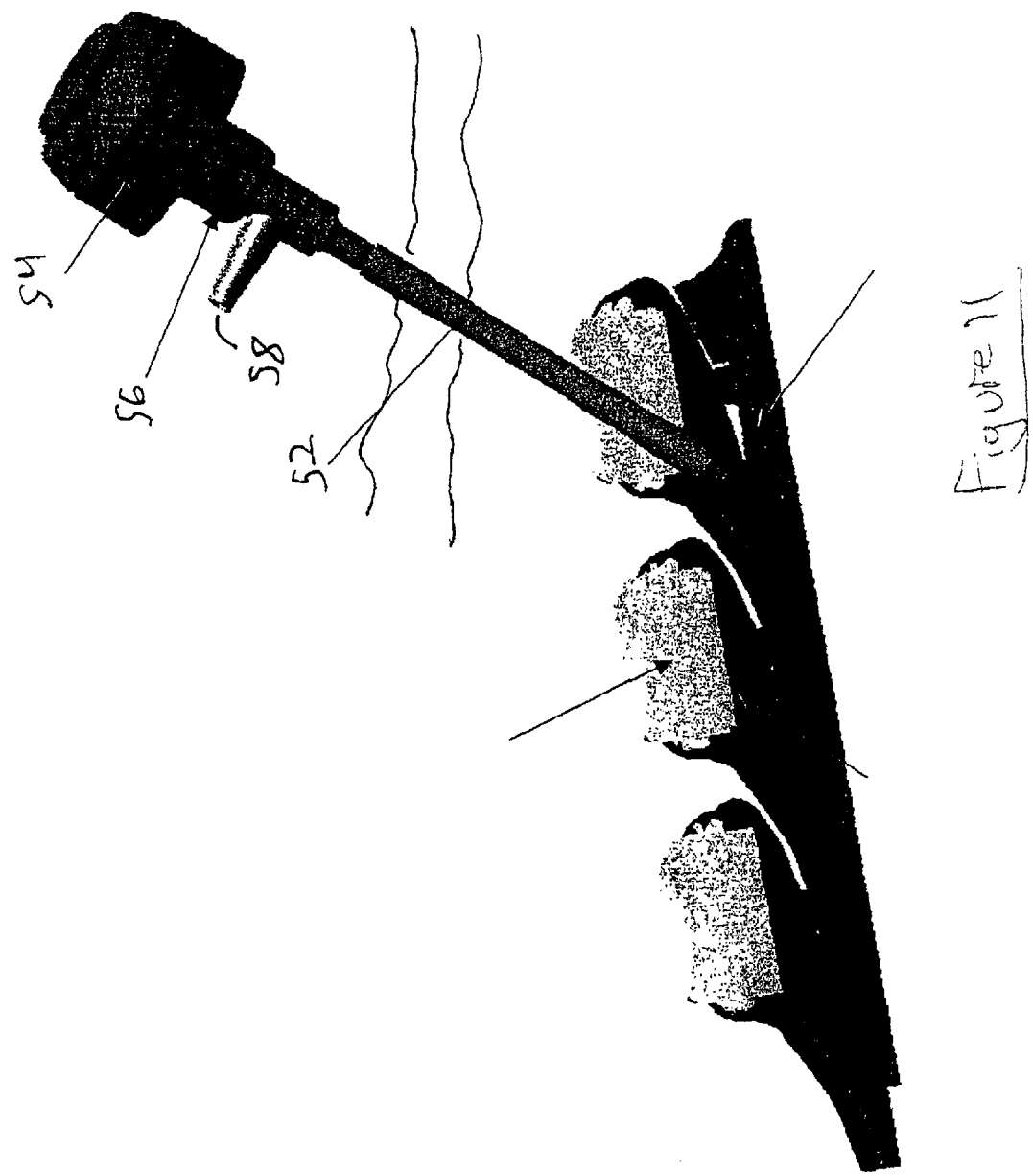

Referring now to FIGS. 9–11, a first exemplary method of use of the hemodialysis port of the present invention is depicted. In FIG. 9, and assuming that the port 10 has been properly inserted into a patient, as is understood by one skilled in the art, a needle 50 and sheath 52 are inserted into one of the chambers, e.g., 8C, through the skin. In FIG. 10, the needle 50 is removed leaving only the sheath 52 remaining in the chamber of the device 10. In FIG. 11, a cannula or obturator 54 is inserted into the sheath. The obturator may comprise a hub section 56 and may further include an ingress/egress port 58 to draw bodily fluids from within the chamber 8C or to insert medicament into said chamber. Generally, in the hemodialysis art, port 58 will be utilized to draw blood through the device so that the blood may be taken to a hemodialysis machine for processing. The blood can likewise be returned to the device and eventually to the body via port 58. The obturator provides consistent blood flow during the hemodialysis process. After the hemodialysis process, the obturator and sheath may be removed (not shown) and the process repeated as required for hemodialysis. One advantage of the process of FIGS. 9–11 is the use of technology that is well known to those in the diagnostics/interventional cardiology art, i.e., the use of a needle, sheath, and cannula/obturator device.

Figure 12:
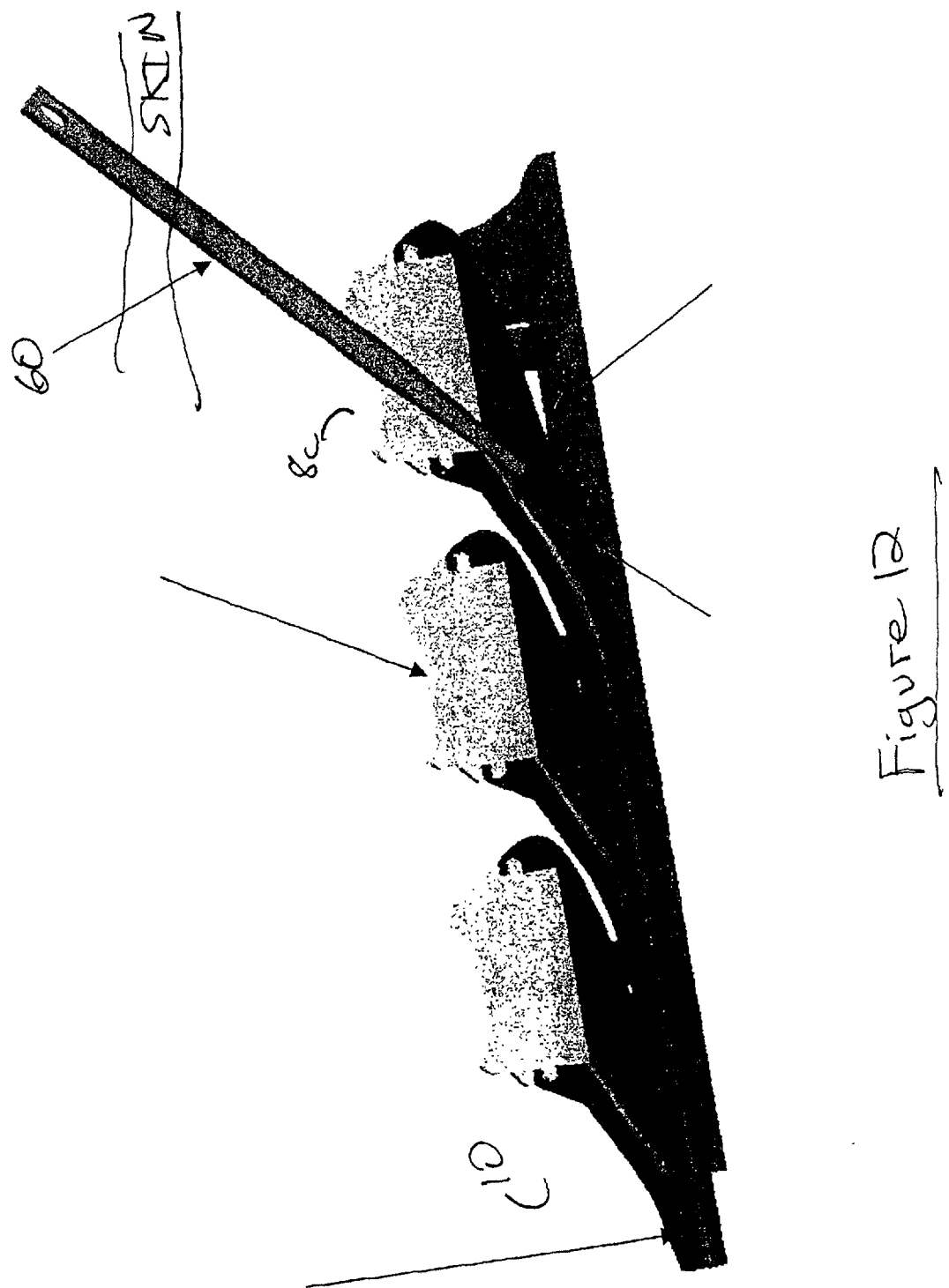
FIGS. 12–16 depict another exemplary method of use for the hemodialysis port of the present invention.
Figure 13:
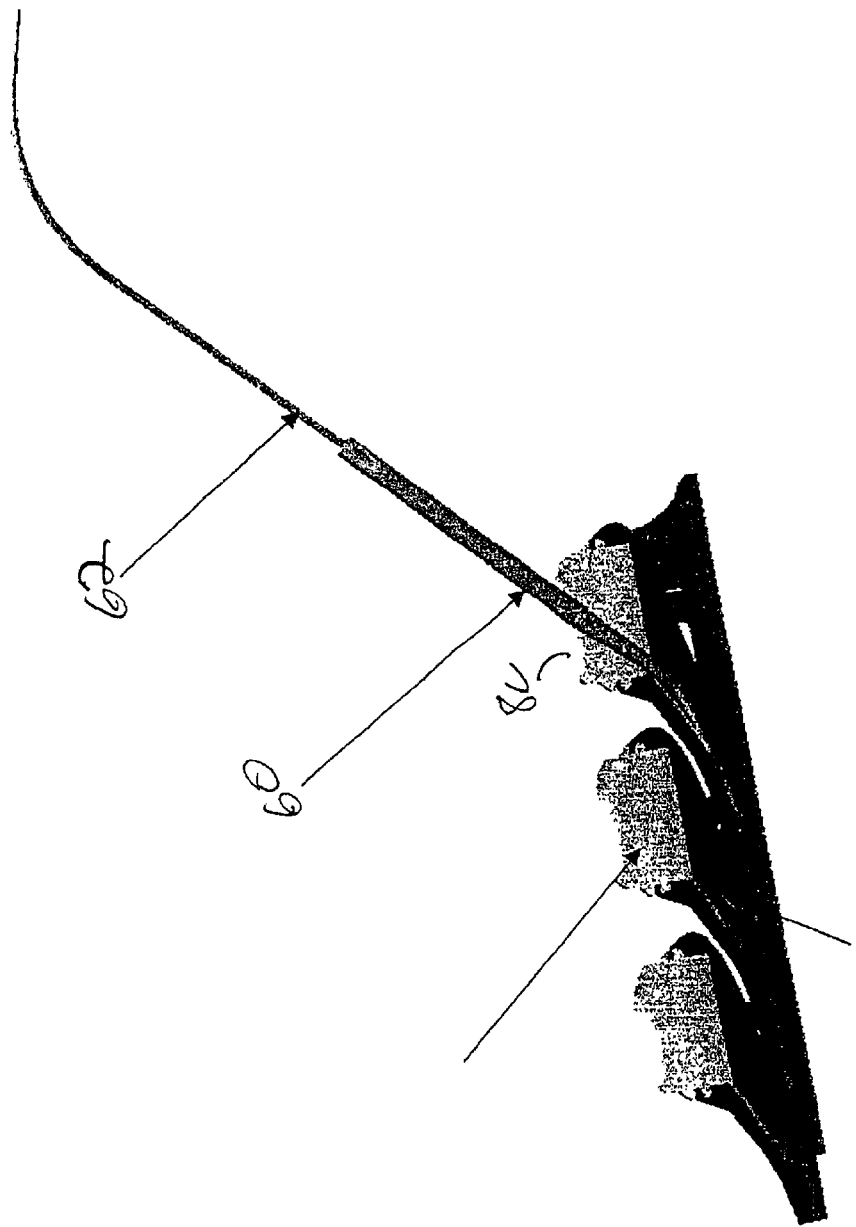
Figure 14:
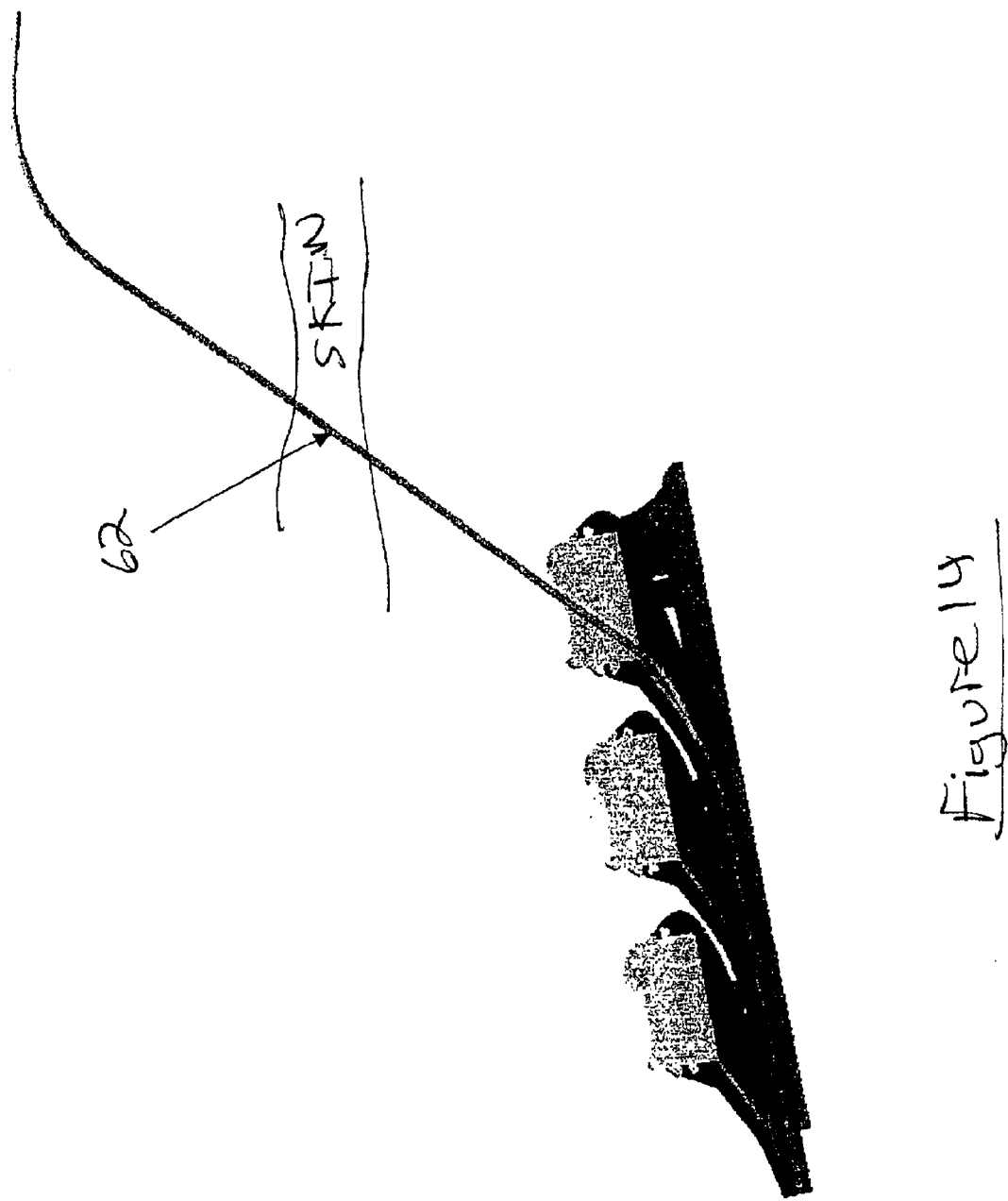
Figure 15:
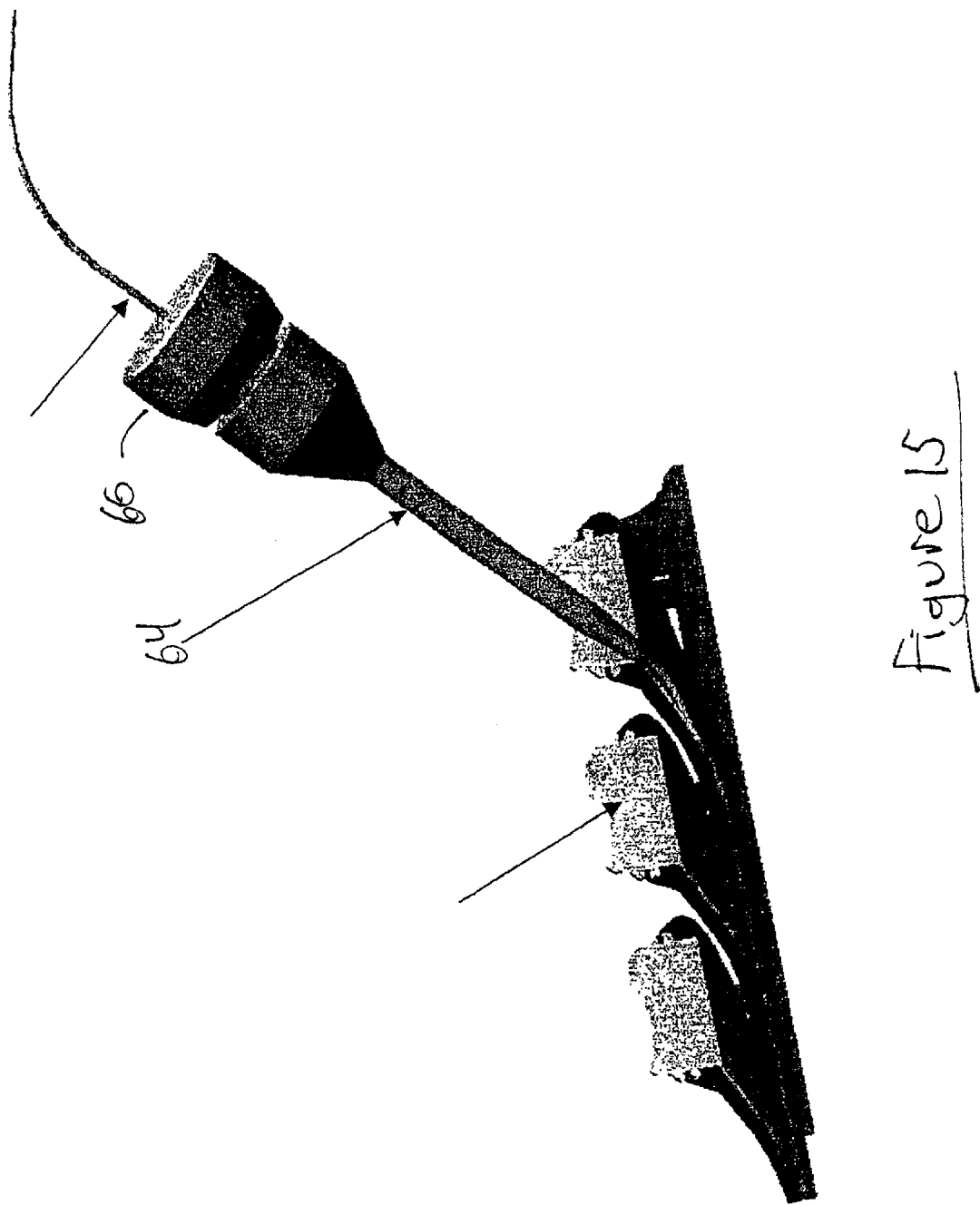
Figure 16:
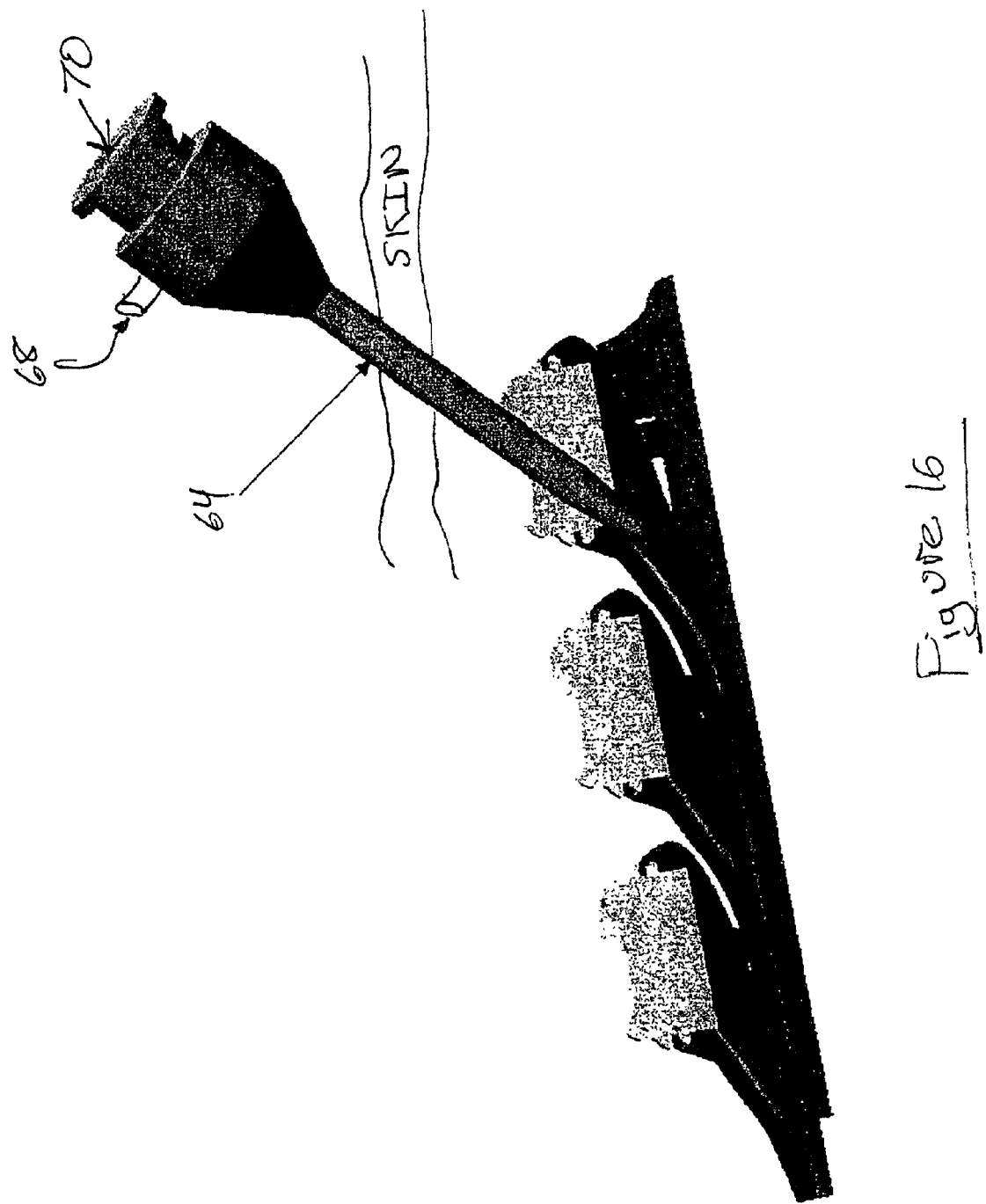

FIGS. 12–16 depict a second exemplary method of use of the hemodialysis port of the present invention. As with the previous exemplary method of use of FIGS. 9–11, the port 10 is implanted into a region, for example, just below the breast. In typical applications, two ports are implanted on either side of the body. For hemodialysis applications, the ports are connected to the aorta for inflow and outflow to the dialysis equipment. In FIG. 12, a needle 60 (e.g., Huber needle) is inserted through the septum of the port assembly, as shown. In FIG. 13 a guidewire 62 is inserted through the needle 60 into the port assembly. In FIG. 14, the needle 60 is removed, leaving only the guidewire in the port assembly as a reference point. FIG. 15 depicts insertion of an introducer 64 over the guidewire, through the skin and into the septum. As is understood by those skilled in the art, the introducing cannula 64 is sufficient rigid axially to be inserted through the skin and into the port through the septum. The introducer may comprise a hub 66 for application of a dilator. FIG. 16 depicts the hub 66 to remove exposing an opening 70 for insertion of a dilator. FIG. 16 also depicts an ingress/egress port 68, which operates similar to port 58 shown in FIG. 11. Once the dialysis process is over the introducing cannula 64 and guidewire 62 may be removed.

Thus, it is apparent that there has been provided an implantable multiple port vascular access device that satisfies the objectives set forth herein. Those skilled in the art will recognize that the present invention is subject to modification and/or alterations, all of which are deemed within the scope of the present invention, as defined in the appending claims.

What is claimed is:

1. A hemodialysis port comprising:

a housing defining a plurality of interconnected chambers, each said chamber having a bottom portion and sidewall portions and integrated passageway providing interconnection of said chambers; each said chamber further comprising a funnel portion tapering from said sidewall portions and said bottom portions a septum attached to said side wall portions of each said chamber enclosing said chamber; and a spring mechanism disposed between said sidewalls and said septum and applying an inward force on said septum.

2. A port as claimed in claim 1, wherein said spring mechanism having sufficient force to close an opening in said septum caused by a needle or other medical instrument.

3. A port as claimed in claim 1, said bottom portion further comprising a titanium insert covering at least a portion of said bottom portion of said port.

4. A port as claimed in claim 1, wherein said housing comprising a flexible material having a flexibility for a particular patient's anatomical structure.

5. A port as claimed in claim 1, wherein said septum comprising silicon rubber.

6. A port as claimed in claim 1, wherein said chambers are connected together to a manifold to provide a single inlet/outlet to and from said chambers.

* * * * *